Figure 1:
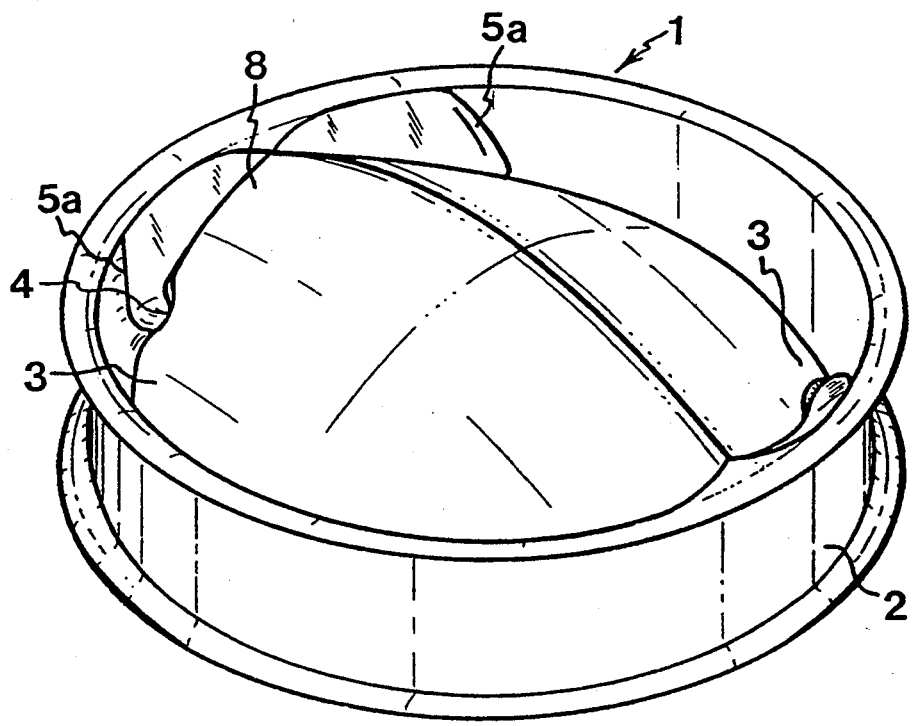

United States Patent [19]
Olin

[11] Patent Number: 5,405,381
[45] Date of Patent: Apr. 11, 1995

[54] HINGED HEART VALVE PROSTHESIS

[76] Inventor: Christian Olin, Åkersbergsgatan 1B, S-582 52 Linköping, Sweden

[21] Appl. No.: 975,592
[22] PCT Filed: Aug. 9, 1991
[86] PCT No.: PCT/SE91/00532
  § 371 Date: Feb. 9, 1993
  § 102(e) Date: Feb. 9, 1993
[87] PCT Pub. No.: WO92/02197
  PCT Pub. Date: Feb. 20, 1992

[30] Foreign Application Priority Data

Aug. 9, 1990 [SE] Sweden .................... 9002603

[51] Int. Cl.$^6$ ............................... A61F 2/24
[52] U.S. Cl. ........................... 623/2; 137/527
[58] Field of Search ..................... 623/2; 137/527

[56] References Cited

U.S. PATENT DOCUMENTS

| | | | |
|---|---|---|---|
| 4,078,268 | 3/1978 | Possis | 623/2 |
| 5,002,567 | 3/1991 | Bona et al. | 623/2 |
| 5,108,425 | 4/1992 | Hwang | 623/2 |
| 5,116,366 | 5/1992 | Hwang | 623/2 |
| 5,116,367 | 5/1992 | Hwang et al. | 623/2 |
| 5,123,920 | 6/1992 | Bokros | 623/2 |
| 5,192,313 | 3/1993 | Budd et al. | 623/2 |
| 5,197,980 | 3/1993 | Gorshkov et al. | 623/2 |
| 5,236,448 | 8/1993 | Angelini et al. | 623/2 |

FOREIGN PATENT DOCUMENTS 338179  10/1989  European Pat. Off. ......... 623/2

Primary Examiner—David Isabella
Assistant Examiner—Laura Fossum
Attorney, Agent, or Firm—Shapiro and Shapiro

[57] ABSTRACT

A heart valve prosthesis has a substantially annular valve body and two leaflets which are disposed in the valve body and, be means of a hinge mechanism, are pivotable between an open position and a closed position. The leaflets are substantially semicircular and evenly curved in two perpendicular directions, one direction being perpendicular to the diameter of the semicircle, so as to bulge outward, as seen from the center of the annulus. The leaflet edges closest to the diameter of the semicircle are so curved that they, when the valve is closed, are applied against one another along their entire length. Further, two projections are provided on the inside of the annulus, entirely within the width thereof, the corner portions of the leaflets being applied against these projections.

6 Claims, 5 Drawing Sheets

HINGED HEART VALVE PROSTHESIS

The present invention relates to a heart valve prosthesis having an annular valve body and two leaflets which are disposed in said member and, by means of a hinge mechanism, are pivotable between an open position and a closed position.

No conventional heart valve prosthesis meets all the requirements made on such products, which have to function in an extremely reliable manner and withstand the constant wear caused by the heart beats.

Since heart valve prostheses, hereinafter referred to as heart valves, are implanted in a very sensitive and 'cramped' space of the body, it is imperative that they do not damage or get tangled up in the surrounding tissue. Many of today's heart valves suffer from the inconvenience that either the leaflets proper or projections on the annulus protrude too far, so that the risk of surrounding tissue interfering with the valve function is imminent, especially if the valve is used in the mitral position. Projections on the annulus may further hinder the surgeon when implanting the heart valve.

To emulate the function of the natural heart valve, a prosthesis should preferably have a central flow. It should in addition open and close rapidly and quietly, have an insignificant resistance against flow in the forward direction, and cause a minimum of turbulence. The artificial heart valve must of course be biocompatible, i.e. acceptable to the body, and be thrombo-resistant, i.e. not cause or be the residence of thrombosis. From this point of view, it is essential that all surfaces are well flushed by the blood, so that there are no hidden corners where clots may form.

U.S. Pat. No. 4,078,268 discloses a heart valve which has an annulus and two flat, semicircular leaflets. In one embodiment, the hinge is made up of pins projecting from the leaflets and corresponding holes in the annulus. In another embodiment, both the inside of the annulus and the leaflets are formed with projections which make up the hinges of the valve. The downstream side of the annulus is provided with triangular projections on which the leaflets rest when the valve is closed.

U.S. Pat. No. 4,274,437 discloses a heart valve which also has an annulus and two leaflets. These leaflets are sections of a hollow, straight and circular cylinder. The hinge mechanism includes a groove on the inside of the annulus, as well as two projections fitting in the groove and provided one on each leaflet. The projections run freely in the groove, so that the leaflets can rotate in the annulus.

These prior-art valves mainly suffer from the disadvantage that some portions project much too far from the annulus, so that there is a considerable risk that they damage, or are themselves hindered by, the surrounding tissue.

U.S. Pat. No. 4,863,459 discloses another heart valve which has an annulus and two curved semicircular leaflets. This valve has the advantage of not projecting as far as the other two valves described, but it nevertheless has quite a few drawbacks. Above all, it has no central flow and does not close quietly enough.

One object of the invention is to provide a heart valve of this type, which has as low a structural profile as possible, i.e. has a minimum of elements projecting from the annulus, and which will not damage or get tangled up in the surrounding tissue, either in the open or in the closed position. This is achieved by a special design of the leaflets.

Another object of the invention is to provide a heart valve which functions also when mounted in a slightly oblique position relative to the flow direction in the heart. When mounted in this manner, some prior-art heart valves cannot function properly, and as a result one of the leaflets stops working, with disastrous consequences for the patient.

According to the invention, the heart valve prosthesis is characterised in that the leaflets are substantially semicircular, that the leaflets are evenly curved in two perpendicular directions, one direction being perpendicular to the diameter of the semicircle, so as to bulge outward, as seen from the center of the annulus, that the leaflet edges closest to the diameter of the semicircle are so curved that they, when the valve is closed, are applied against one another along their entire length, and that two projections are provided on the inside of the annulus, entirely within the width thereof, the corner portions of the leaflets being applied against said projections when the valve is closed.

One advantage of the heart valve according to the invention is the short path of movement of the leaflets, which is a result of the curved design of the leaflets and the relatively small angle between the closed position and the open position. Thus, the short path of movement contributes to the rapid function and quiet closing of the valve, and also reduces wear on the hinge mechanism. Quiet operation is very desirable, because, to some patients, the 'clicking' sound of a heart valve may be deeply worrysome.

Since the valve closes quietly and wear is distributed over a relatively wide area, the heart valve can be made of metal or materials other than pyrolytic carbon, which is the material most commonly used in today's heart valves. Pyrolyric carbon has many drawbacks, such as being expensive, brittle and invisible on radiographs. A valve made of metal, on the other hand, is much cheaper than a valve made of pyrolytic carbon and can be precision-worked to a much higher degree than a valve of pyrolytic carbon, which is a ceramic material. Finally, the metal surface can be coated with a substance (heparin) preventing thrombosis.

Another advantage is that the heart valve according to the invention can be implanted in all positions owing to its low profile and the fact that it can be easily turned in the suture ring after implantation.

Figure 2:
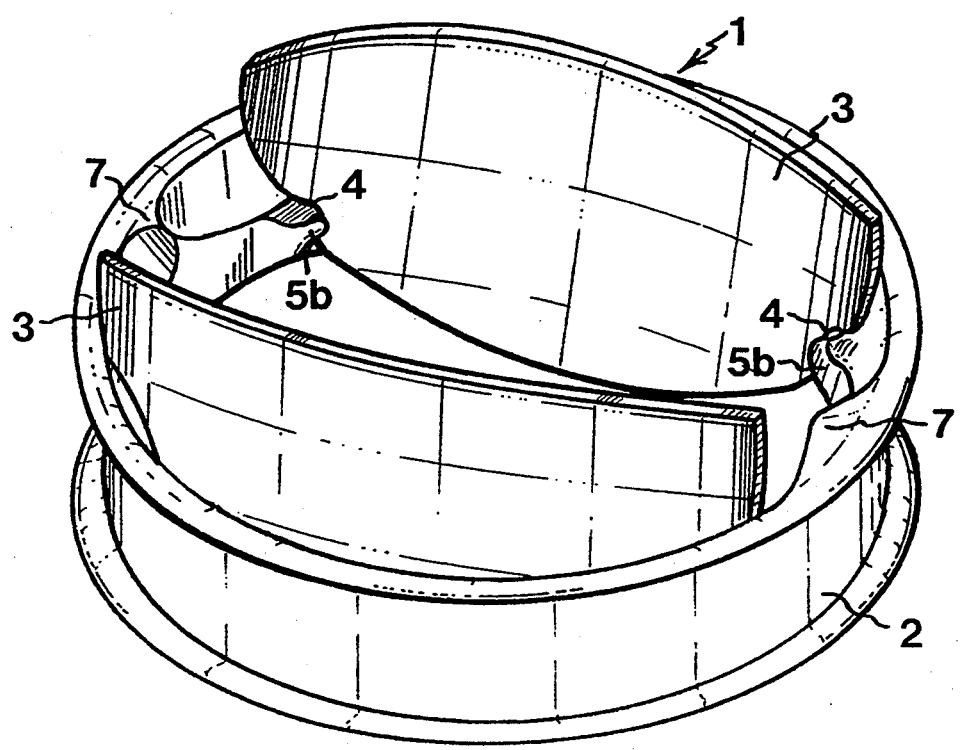
Figure 3:
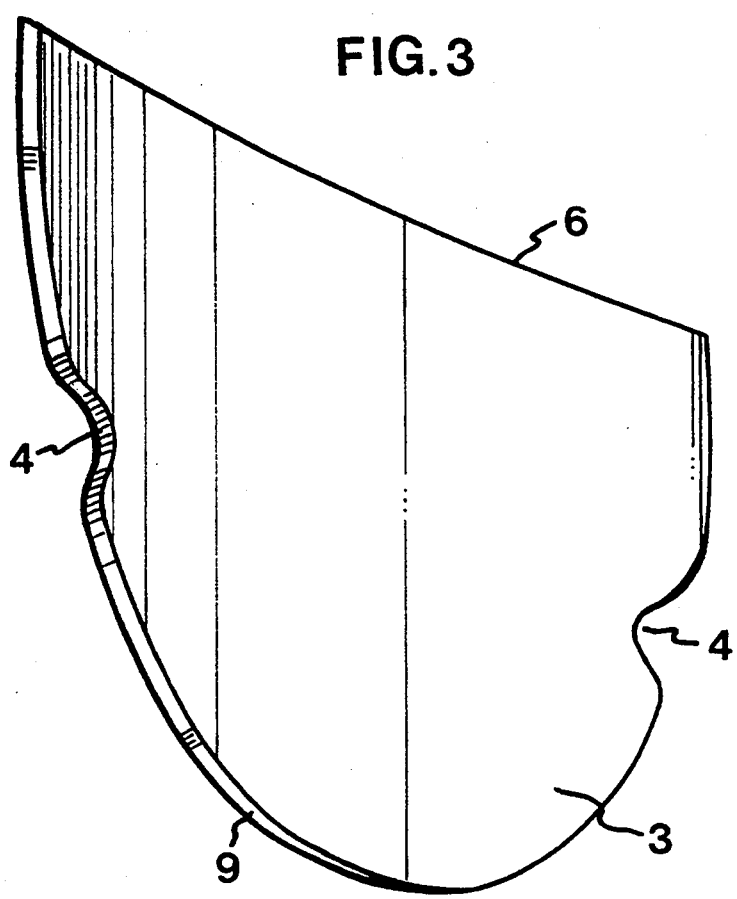
Figure 4:
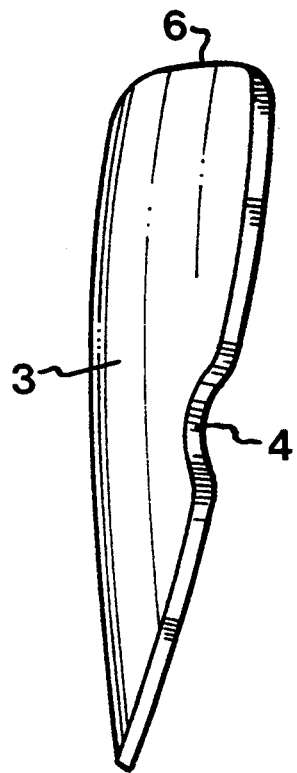
Figure 5:
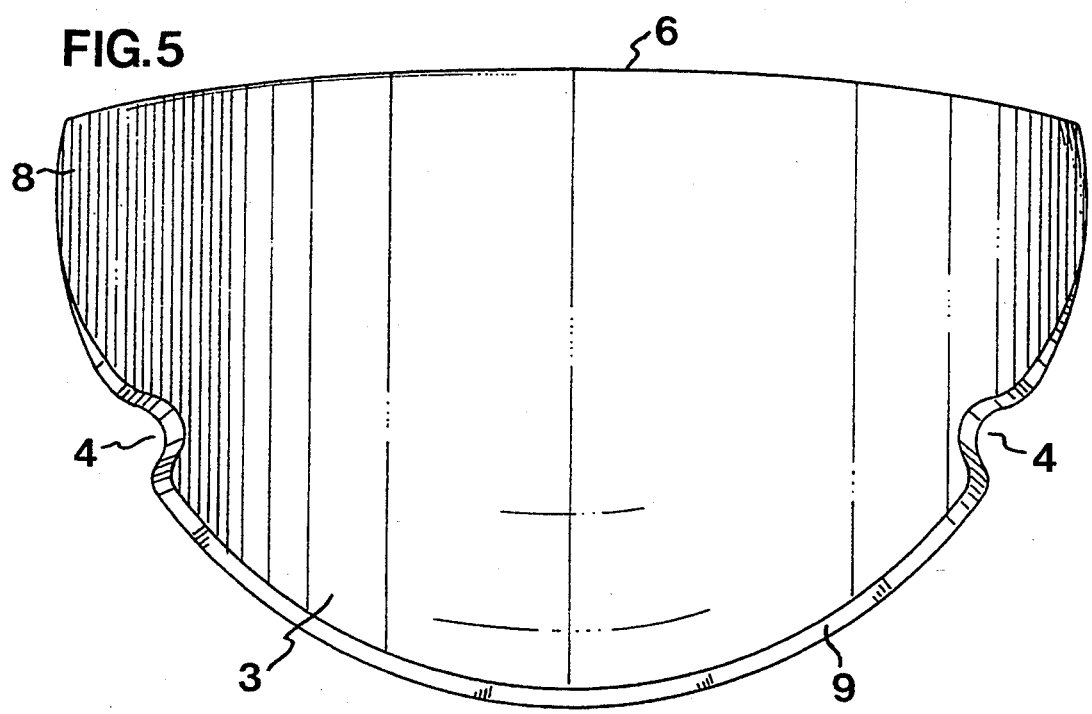
Figure 10:
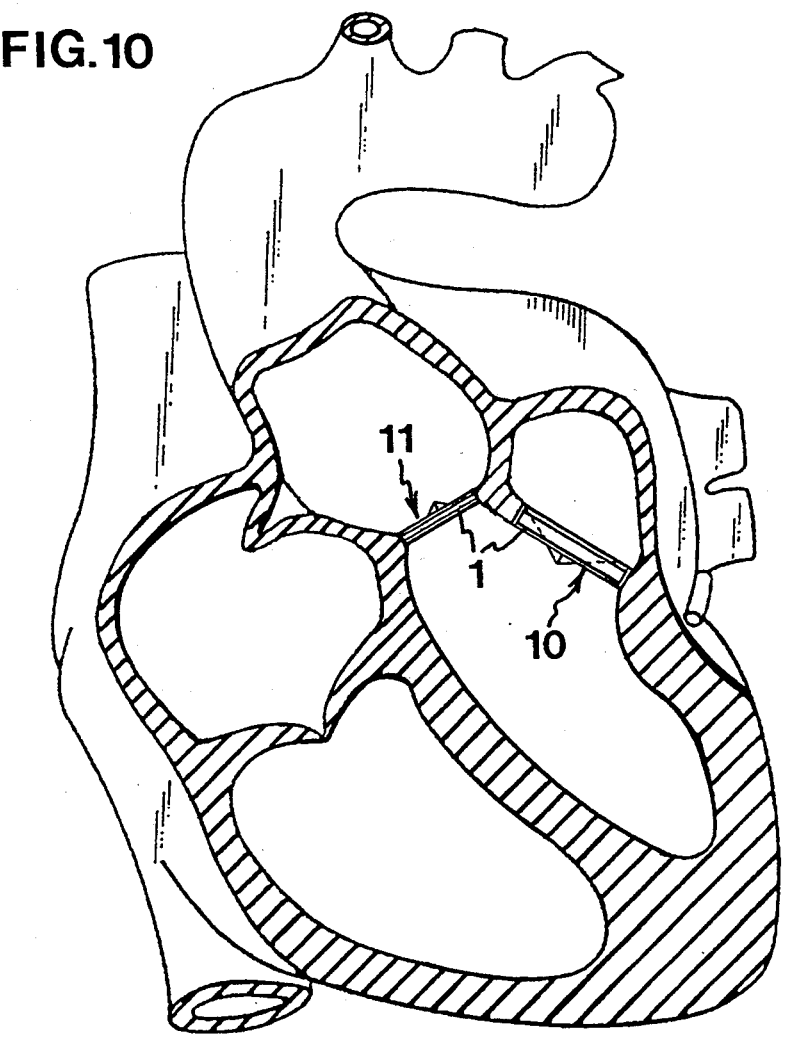
Figure 6:
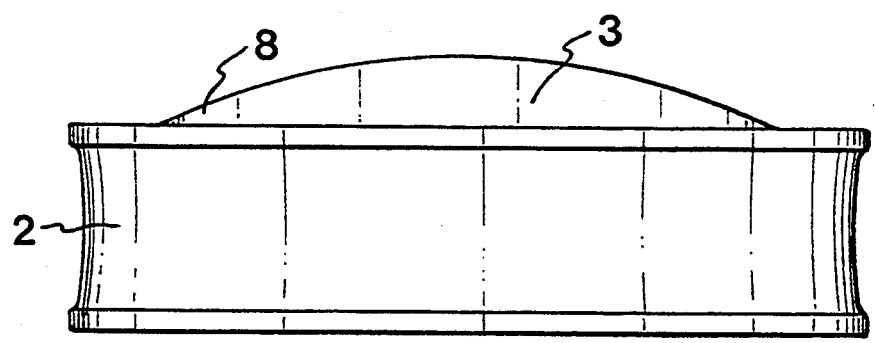
Figure 7:
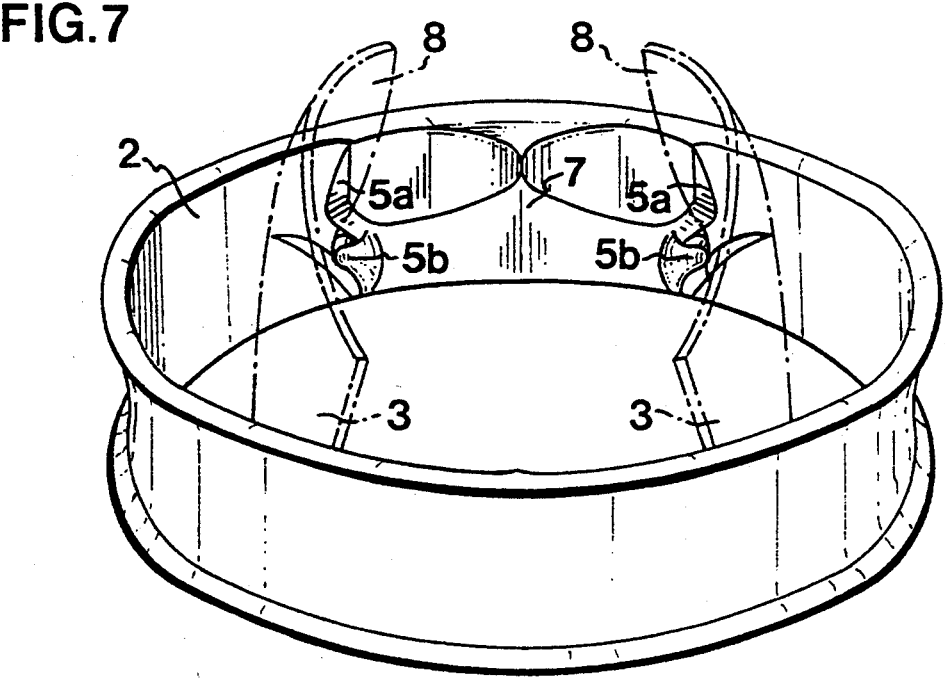
Figure 8:
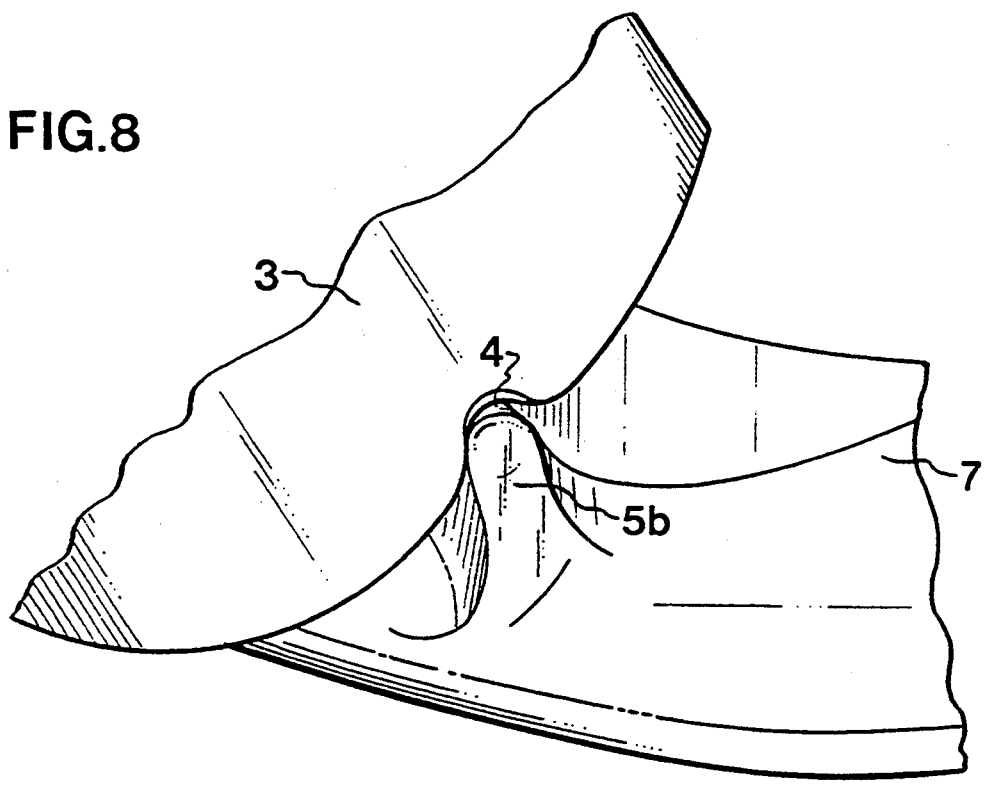
Figure 9:
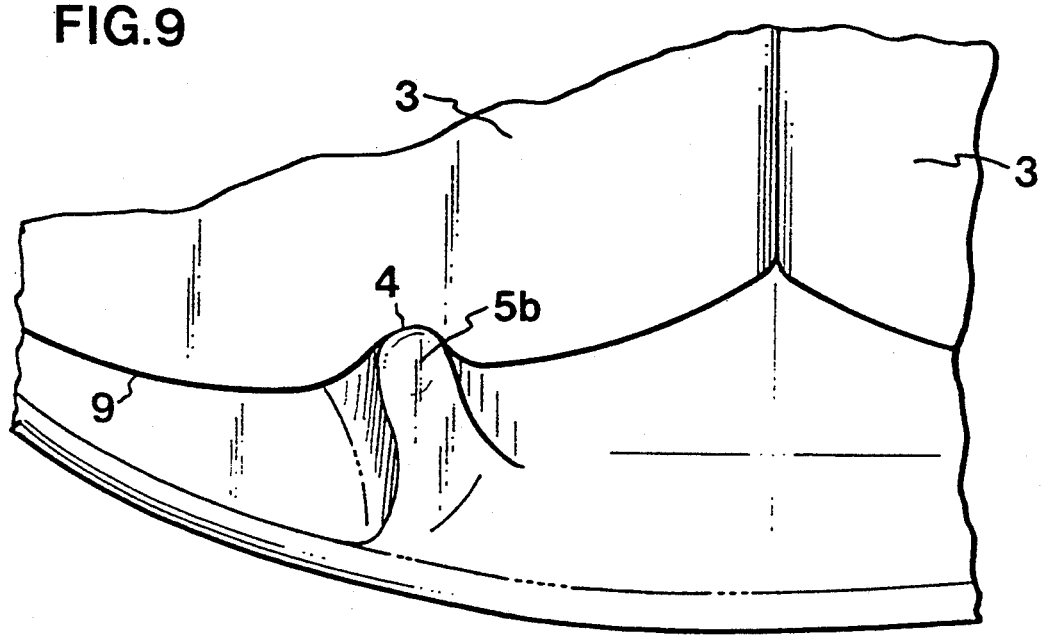

The preferred embodiment of the invention will now be described in more detail below, reference being made to the accompanying drawings, in which FIG. 1 is a perspective view as seen from the downstream side of the heart valve according to the invention when closed, FIG. 2 is a corresponding view of the valve when open, FIGS. 3 and 4 are perspective views of a leaflet, FIG. 5 is a side view of a leaflet, FIG. 6 is a side view of the valve when closed, FIG. 7 shows the open valve from another angle than FIG. 2, FIGS. 8 and 9 illustrate parts of the valve as seen from the upstream side when the valve is open and closed, respectively, and FIG. 10 is a schematic view of the valve in the aortic and the mitral position.

As shown in the drawings, the heart valve 1 has an annulus 2 and two leaflets 3 which are disposed in the annulus and, by means of a hinge mechanism 4, 5a, 5b, are pivotable between an open position and a closed position (see FIGS. 1 and 2). The leaflets 3, which preferably are of equal size, are essentially semicircular, as appears from FIG. 5, and the leaflet edge 6 closest to the diameter of the semicircle is curved. As is apparent from FIGS. 3 and 4, the leaflets are evenly curved in two perpendicular directions, one direction being perpendicular to the diameter of the semicircle. Thus, the leaflets bulge outward, as seen from the center of the annulus. Closest to the diameter of the semicircle, the leaflet edges are so curved that they are applied against one another along their entire length when the valve is closed. Further, the inside of the annulus is formed with two projections 7 which are situated entirely within the width of the annulus and against which the corner portions 8 of the leaflets 3 are applied when the valve is closed.

In the direction of its width, the annulus 2 comprises three sections, the mid-section being circular-cylindrical and the other two sections having the shape of truncated cones widening towards the ends of the annulus. Since the annulus of the invention is of essentially the same construction as that disclosed in U.S. Pat. No. 4,863,459, it will not be described in more detail here.

Owing to the curvature of the leaflets 3 and the leaflet edges 6 as well as the provision of the projection 7, the corner portions 8 of the leaflets will not be as pointed and project as far as when flat and semicircular leaflets are used. As illustrated in FIG. 2, the leaflets 3 only project a short distance from the annulus 2 on the downstream side when the valve is open, and do not at all project beyond the envelope surface of an imaginary cylindrical extension of the annulus. On the upstream side, the semicircular leaflet edges 9 only project very slightly from the annulus.

As illustrated in FIG. 6, the leaflets 3 do not at all project beyond the annulus 2 on the upstream side when the valve is closed, and only project at the center portion of the annulus on the downstream side. With this construction, there is practically no risk at all that the heart valve may damage, or get tangled up in, the surrounding tissue.

Tests have shown that the leaflet curvature should be more pronounced (greater) in the transversal direction and be in the range of 1:6–1:10, and less pronounced in the longitudinal direction where it should be in the range of 1:25–1:35. These figures are based on the ratio between, on the one hand, the distance between a line drawn between the leaflet side edges and the leaflet upper and lower edges, respectively, and the leaflet crest, and, on the other hand, the distance between the leaflet side edges and the leaflet upper and lower edges, respectively, along said line.

As shown in FIGS. 1 and 2 as well as FIGS. 7–9, the hinge mechanism of the heart valve according to the invention includes two spaced-apart recesses 4 formed in the semicircular edge 9 of the leaflets 3, and a pair of projections 5a, 5b corresponding to the recesses and provided on the inside of the annulus. The surface of the leaflet portion moving downstream when the prosthesis is opened, is approximately twice as large as that moving upstream. The projections 5a, 5b—streamlined so as not to cause too much turbulence—are slightly off-set in relation to one another, in both cases relative to the center plane of the annulus and an imagined vertical line at each hinge. The projection 5a closest to the downstream side of the annulus extends substantially from the middle of the annulus obliquely towards the projection 7 in the downstream direction, and constitutes an abutment for the leaflet 3 when the valve is open.

The inverse hinge construction, i.e. with recesses in the annulus and projections on the leaflets, is, however, not outside the scope of the invention. In any case, it is preferred that the hinge mechanism is so positioned that about ⅔ of the leaflet surface is situated above an imagined axis through the hinge, and about ⅓ thereof is situated below said axis (on the influx side).

As appears most clearly from FIG. 2, the heart valve 1 opens at the center, so that the major part of the flow passes between the leaflets 3, thereby emulating the function of the natural heart valve. Preferably, the hinges 4, 5a, 5b are so positioned that about 70% of the flow passes between the leaflets 3, i.e. through the central opening.

When the valve is open, the leaflets 3 form an angle of about 75–86° with the annulus 2. The angle is measured between the plane of the annulus and an imagined line between the uppermost and the lowermost point of the leaflet. The valve 1 may have different opening angles, e.g. about 80–85°, but preferably has an opening angle of about 85°. When the valve is closed, the leaflet still forms an angle with the annulus, which is about 25–35°.

Owing to the short path of movement between the open and the closed position (a result of the curved design of the leaflets 3 and the relatively small angle between the open and the closed position) the valve 1 closes quietly. If the leaflets were to open too widely, i.e. form too large an angle with the annulus 2 in the open position, the blood would have time to accelerate back when the valve closes, and would then entrain the leaflets which at a high speed would strike the annulus 2. The more gently the leaflet is applied against the annulus 2, the lower is the sound level and the less is the wear on the heart valve. The leaflet curvature as well as the opening angle of the heart valve contribute to a gentle return of the leaflets, so that the sound level and the wear are maintained at a low level. This makes it possible to manufacture the outer valve from metal, with all the ensuing advantages.

Another important parameter in the construction of heart valves is turbulence. It is imperative that the entire heart valve including the annulus 2 and the leaflets have a construction involving a minimum of turbulence. If the turbulence is too pronounced, the leaflets may come to 'flutter' in the open position, which may increase corpuscle decomposition. To minimize turbulence, the tangent of each leaflet 3 of the heart valve 1 halfway between the projections 7 in the open position of the valve is parallel to the annulus 2 where the distance between the leaflet 3 and the annulus 2 is the smallest. As a result, the tangent is parallel also to the flow direction where the highest velocity of the blood is to be expected.

The projections 7, against which the corner portions 8 of the leaflets are applied when the valve is closed, are also designed for minimal turbulence. As seen from the center of the annulus 2 in FIG. 7, the projections 7 have essentially the shape of an isosceles triangle, the apex between the equal sides being directed downstream, so that the corner portions 8 of the leaflets can be applied against the projections 7 without any leakage. The equal sides extend all the way to the hinge projections 5b. Since the heart valve 1 should be as compact as possible, the projections 7 do not protrude beyond the width of the annulus 2.

In FIGS. 8 and 9, the valve is shown as seen from the upstream side when open and closed, respectively. FIG. 9 illustrates that the semicircular leaflet edge 9, when the valve is closed, is applied against the inside of the annulus 2, that the recess 4 in the leaflet 3 is sealingly applied against the hinge projection 5b of the annulus 2, and that the corner portion 8 of the leaflet is applied against the projection 7 of the annulus 2. When the valve is open, as shown in FIG. 8, the leaflet can move slightly in the flow direction, the hinge mechanism having a play to promote effective flushing thereof.

The heart valve according to the invention is suitably implanted in the aortic as well as the mitral position, and may also be used in the pulmonary and the tricuspid position, if required. The aortic position 11 and the mitral position 10 are shown in FIG. 10. It should be observed that when the valve is used in the mitral position, the leaflets on the downstream side move in the same direction as the valve leaflets of the natural mitral valve. Thus, the valve prosthesis according to the invention can be used even if parts of or the entire mitral-valve assembly is retained, which results in an improved heart function after the operation. The blood flow is more rapid in the aortic position 11 than in the mitral position 10, so that heart valves of different sizes and opening angles may have to be implanted in the two positions. However, the heart valve according to the invention can be used in all of the positions mentioned above.

For anatomical reasons, it may at times be necessary to implant the heart valve 1 in a slightly oblique position relative to the blood flow. With the heart valve according to the invention, this is easily done, since the curvature of the leaflets enables the heart valve according to the invention to function also if mounted in such an oblique position.

To enable implantation in the heart, the heart valves mounted in a so-called suture ring. The heart valve 1 according to the invention can be turned in the suture ring 2 also after the implantation. Further, the projections 7 form two parallel surfaces which are perpendicular to the plane of the annulus 2 and which can be engaged by a tool for turning the heart valve in the suture ring. This can be done because of the compact design of the heart valve, leaving no projections which may damage the surrounding tissue.

I claim:

1. A heart valve prosthesis, comprising:
   an annular valve member; and
   two substantially semicircular leaflets supported in said annular valve member by a hinge mechanism so as to be pivotable between an open position and closed position,
   each leaflet being evenly curved in two orthogonal directions, one of which is perpendicular to a diameter of the leaflet, such that said leaflets bulge in an outward direction relative to a center of said annular valve member and abut one another along an entire length of respective diametral edges thereof when in a closed position,
   said hinge mechanism having hinge members including a pair of spaced-apart recesses and a cooperating pair of hinge projections for each leaflet, said pair of projections being disposed on one of an inside of said annular valve member and a semicircular edge of the leaflet, and said pair of recesses being disposed on the other of said inside of said annular valve member and said semicircular edge of the leaflet, said hinge members being positioned such that said leaflets open in said outward direction and allow at least 70% of a bloodflow through said annular valve member to pass therebetween; and
   a pair of substantially isosceles-triangle-shaped sealing projections disposed entirely within a width of said annular valve member so as to sealingly abut corner portions of said leaflets near opposite ends of said diametral edges of said leaflets when said leaflets are in said closed position, with a respective apex between equal sides of each sealing projection being directed in said outward direction and said equal sides extending substantially to two of said hinge members formed on said inside of said annular valve member.

2. A heart valve prosthesis according to claim 1, wherein a respective line connecting points of extremity of each leaflet along an axis of said annular valve member when said leaflets are in said open position forms an angle of about 75–86° with respect to a plane of said annular valve member.

3. A heart valve prosthesis according to claim 1, wherein said annular valve member has three widthwise sections including a cylindrical mid-section and two oppositely outwardly widening truncated-cone-shaped end sections.

4. A heart valve prosthesis according to claim 3, wherein a tangent of each leaflet at a point mid-way between said sealing projections and closest to said annular valve member when said leaflets are in said open position is parallel to an axis of said annular valve member.

5. A heart valve prosthesis according to claim 1, wherein curvature of each leaflet is greater transversely of the leaflet than longitudinally of the leaflet.

6. A heart valve prosthesis according to claim 1, wherein said hinge members are positioned such that $\frac{2}{3}$ of a surface of each leaflet is situated to one side of a hinge axis of the leaflet towards said outward direction, and $\frac{1}{3}$ thereof is situated to an opposite side of the hinge axis toward a direction opposite to said outward direction.

* * * * *